(12) United States Patent
Waddell et al.

(10) Patent No.: US 9,566,354 B2
(45) Date of Patent: Feb. 14, 2017

(54) SYSTEMS AND METHODS OF PERFORMING NMR SPECTROSCOPY AND MRI

(71) Applicant: Vanderbilt University, Nashville, TN (US)

(72) Inventors: Kevin Waddell, Hendersonville, TN (US); Chong Cai, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 691 days.

(21) Appl. No.: 13/998,342

(22) Filed: Oct. 23, 2013

(65) Prior Publication Data

US 2014/0112870 A1   Apr. 24, 2014

Related U.S. Application Data

(60) Provisional application No. 61/717,518, filed on Oct. 23, 2012.

(51) Int. Cl.
*A61K 49/06* (2006.01)
*G01R 33/46* (2006.01)

(52) U.S. Cl.
CPC ........... *A61K 49/06* (2013.01); *G01R 33/4608* (2013.01)

(58) Field of Classification Search
CPC .................. A61K 49/06; G01R 33/4608
See application file for complete search history.

(56) References Cited

U.S. PATENT DOCUMENTS

| 6,574,495 B1 | 6/2003 | Golman et al. |
|---|---|---|
| 6,872,380 B2 | 3/2005 | Axelsson et al. |
| 2011/0095759 A1* | 4/2011 | Bhattacharya ......... A61B 5/055 324/307 |

FOREIGN PATENT DOCUMENTS

WO   2012/145733   10/2012

OTHER PUBLICATIONS

Adams, et al., "Reversible Interactions with para-Hydrogen Enhance NMR Sensitivity by Polarization Transfer," Science 2009, 323, 1708-1711.

(Continued)

*Primary Examiner* — G. M. Hyder
(74) *Attorney, Agent, or Firm* — Michael Best & Friedrich LLP

(57) ABSTRACT

A method of performing Nuclear Magnetic Resonance (NMR) spectroscopy or Magnetic Resonance Imaging (MRI). The methods may include: a) generating a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$; b) transferring the nuclear singlet state spin order into heteronuclear magnetization localized on S by applying a single, non-recursive pulse sequence at a low magnetic field in the strong coupling regime of protons; and c) performing NMR spectroscopy or MRI with the compound comprising heteronuclear magnetization localized on S. The $|J_{1S}-J_{2S}|$ may be non-zero. The pulse sequence may include a plurality of sequential radio frequency pulses separated by independent evolution interval. The pulse sequence may be capable of transferring at least about 75% of the nuclear singlet state spin order into heteronuclear magnetization localized on S at any $|J_{1S}-J_{2S}|$ when the independent evolution intervals are optimized.

17 Claims, 8 Drawing Sheets

(56) References Cited

OTHER PUBLICATIONS

Albers, et al., "Hyperpolarized 13C Lactate, Pyruvate, and Alanine: Noninvasive Biomarkers for Prostate Cancer Detection and Grading," Cancer Res 2008, 68, 8607-8615.

Ardenkjaer-Larsen, et al., "Increase in signal-to-noise ratio of >10,000 times in liquid-state NMR," Proceedings of the National Academy of Sciences of the United States of America 2003, 100, 10158-10163.

Bowers, "Parahydrogen and Synthesis Allow Dramatically Enhanced Nuclear Alignment," Journal of the American Chemical Society 1987, 109, 5541-5542.

Bowers, et al., "Transformation of Symmetrization Order to Nuclear-Spin Magnetization by Chemical Reaction and Nuclear Magnetic Resonance," Physical Review Letters 1986, 57, 2645-2648.

Carver et al., "The Dependence of the 33-Mev Pi+ Production Cross Section on Atomic Number," Slichter, C. P. Physical Review 1953, 92, 212-214.

Carver, "Experimental Verification of the Overhauser Nuclear Polarization Effect," Physical Review 1956, 102, 975-981.

Chekmenev, et al., "PASADENA Hyperpolarization of Succinic Acid for MRI and NMR Spectroscopy," J Am Chem Soc 2008, 130, 4212-4213.

Coffey, et al., "A large volume double channel 1H-X RF probe for hyperpolarized magnetic resonance at 0.0475 T," Journal of Magnetic Resonance 2012, 220, 94-101.

Day et al., "Detecting tumor response to treatment using hyperpolarized 13C magnetic resonance imaging and spectroscopy," Nat Med 2007, 13, 1382-1387.

Feng, et al., "A pulsed injection parahydrogen generator and techniques for quantifying enrichment," Journal of Magnetic Resonance 2012, 214, 258-262.

Goldman, et al., "Conversion of a proton pair para order into 13C polarization by rtirradiation, for use in MRI," Comptes Rendus Physique 2005, 6, 575-581.

Goldman, et al., "Hyperpolarization of 13C through order transfer from parahydrogen: A new contrast agent for MRI," Magn Reson Imaging 2005, 23, 153-157.

Golman, et al., "Metabolic Imaging and Other Applications of Hyperpolarized 13C1," Acad Radiol 2006, 13, 932-942.

Golman, et al., "Metabolic Imaging by Hyperpolarized 13C Magnetic Resonance Imaging for In vivo Tumor Diagnosis," Cancer Res 2006, 66, 10855-10860.

Green, et al., "The theory and practice of hyperpolarization in magnetic resonanceusing parahydrogen," Progress in Nuclear Magnetic Resonance Spectroscopy 2012, 1-48.

Kadlecek, et al., "Optimal transfer of spin-order between a singlet nuclear pair and a heteronucleus," Magn Reson 2011, 205, 9-13.

Morris, "Enhancement of Nuclear Magnetic Resonance Signals by Polarization Transfer," Journal of the American Chemical Society 1979, 101, 760-762.

Muller, "Sensitivity Enhanced Detection of Weak Nuclei Using Heteronuclear Multiple Quantum Coherence," Journal of the American Chemical Society 1979, 101, 4481-4484.

Natterer, et al., "Parahydrogen induced polarization," Progress in Nuclear Magnetic Resonance Spectroscopy 1997, 31, 293-315.

Overhauser, "Polarization of Nuclei in Metals," Physical Review 1953, 92, 411-415.

Sorensen, et al., "Product Operator Formalism for the Description of NMR Pulse Experiments," Progress in Nuclear Magnetic Resonance Spectroscopy 1983, 16, 163-192.

Theis, et al., "Zero-Field NMR Enhanced by Parahydrogen in Reversible Exchange," Journal of the American Chemical Society 2012, 134, 3987-3990.

Waddell, et al., "In Situ Detection of PHIP at 48 mT: Demonstration Using a Centrally Controlled Polarizer," J. Am. Chem. 2011, 133, 97-101.

Zacharias, et al., "Real-Time Molecular Imaging of Tricarboxylic Acid Cycle Metabolism in Vivo by Hyperpolarized 1-13C Diethyl Succinate," Journal of the American Chemical Society 2012, 134, 934-943.

* cited by examiner

SYSTEMS AND METHODS OF PERFORMING NMR SPECTROSCOPY AND MRI

CROSS-REFERENCE TO RELATED APPLICATIONS

This patent application claims priority to U.S. Provisional Patent Application No. 61/717,518 filed Oct. 23, 2012, the content of which is incorporated herein by reference in its entirety.

GOVERNMENT LICENSE RIGHTS

This invention was made with government support from ICMIC 5P50 CA128323-03. The United States federal government has certain rights in this invention.

REFERENCE TO A COMPUTER PROGRAM LISTING APPENDIX

A computer program listing appendix is included with this application and the entire contents of the computer program listing appendix is incorporated herein by reference. The appendix includes duplicate compact discs each containing a single file entitled "function_tau-_hs4.txt", which was created on Oct. 22, 2013 and is 12,213 bytes in size.

BACKGROUND

Hyperpolarization of nuclear spin ensembles has increased NMR sensitivity to a level that is now enabling detection of metabolism in biological tissue on a time-scale of seconds. See, Ardenkjaer-Larsen, J. H.; Fridlund, B.; Gram, A.; Hansson, G.; Hansson, L.; Lerche, M. H.; Servin, R.; Thaning, M.; Golman, K. *Proceedings of the National Academy of Sciences of the United States of America* 2003, 100, 10158-10163; and Golman, K.; Zandt, R. I.; Lerche, M.; Pehrson, R.; Ardenkjaer-Larsen, J. H. *Cancer Res* 2006, 66, 10855-60, each of which is incorporated herein in its entirety by reference. The most developed of these technologies, dynamic nuclear polarization ("DNP", see, Carver, T. R.; Slichter, C. P. *Physical Review* 1953, 92, 212; Carver, T. R.; Slichter, C. P. *Physical Review* 1956, 102, 975; and Overhauser, A. W. *Physical Review* 1953, 92, 411, each of which is incorporated herein in its entirety by reference.), in particular has already been used to detect, grade, and monitor response to therapy in tumors. See, Albers, M. J.; Bok, R.; Chen, A. P.; Cunningham, C. H.; Zierhut, M. L.; Zhang, V. Y.; Kohler, S. J.; Tropp, J.; Hurd, R. E.; Yen, Y. F.; Nelson, S. J.; Vigneron, D. B.; Kurhanewicz, J. *Cancer Res* 2008, 68, 8607-15; Day, S. E.; Kettunen, M. I.; Gallagher, F. A.; Hu, D. E.; Lerche, M.; Wolber, J.; Golman, K.; Ardenkjaer-Larsen, J. H.; Brindle, K. M. *Nat Med* 2007, 13, 1382-7; and Golman, K.; Petersson, J. S. *Acad Radiol* 2006, 13, 932-42, each of which is incorporated herein in its entirety by reference. These encouraging developments have demonstrated the overall viability of NMR based hyperpolarized methods for the study of in vivo metabolism, and are spurring development in alternative methods of hyperpolarization, such as parahydrogen induced polarization (PHIP). See, Adams, R. W.; Aguilar, J. A.; Atkinson, K. D.; Cowley, M. J.; Elliott, P. I.; Duckett, S. B.; Green, G. G.; Khazal, I. G.; Lopez-Serrano, J.; Williamson, D. C. *Science* 2009, 323, 1708-11; and Bowers, C. R.; Weitekamp, D. P. *Phys Rev Lett* 1986, 57, 2645-2648, each of which is incorporated herein in its entirety by reference. Polarization yields from the less mature PHIP technology are similar to DNP, and are achieved at significantly reduced instrumental complexity and expense.

Efficient methods for transforming parahydrogen spin order into heteronuclear magnetization at low field in arbitrary spin systems are necessary in particular, for translating emerging contrast agents to biomedical applications. Whereas in DNP polarization is obtained directly on heteronuclei with long lifetimes (at cryogenic temperature), hyperpolarization from PASADENA is captured (at room temperature) in the form of nascent parahydrogen singlet-states, formed upon molecular addition of parahydrogen to an unsaturated carbon-carbon bond. The evolution of this initial ordered ensemble customarily depends on the relative strength of the static magnetic field with respect to the internal scalar couplings. At zero field where chemical shift differences vanish, the combined influence of short and long range scalar couplings lead to a time-dependent dispersion of parahydrogen spin order across the molecule, and therefore an inevitable loss of polarization for any single component of spin active isotopes (e.g. $^{13}C$). See, Theis, T.; Ledbetter, M. P.; Kervern, G.; Blanchard, J. W.; Ganssle, P. J.; Butler, M. C.; Shin, H. D.; Budker, D.; Pines, A. *Journal of the American Chemical Society* 2012, 134, 3987-3990, which is incorporated herein in its entirety by reference. This is an advantage for the emerging applications of high resolution studies at zero field, but is less well suited to in vivo studies because polarization on any single channel of spin-active isotope (e.g. $^{13}C$) is exchanged for detailed information regarding long range scalar couplings, which are unnecessary to reconstruct conversion rates across at most two reaction pathways. At high field, the truncation of transverse components in the initial parahydrogen density matrix decreases nominal efficiency by 50%. See, Bowers, C. R.; Weitekamp, D. P. *Physical Review Letters* 1986, 57, 2645-2648, which is incorporated herein in its entirety by reference. The intermediate strong coupling regime appears to offer a favorable middle ground for PHIP between high and zero fields, where the density operator is retained without truncation and where resonant fields can be used to selectively manipulate spin evolution.

Determining the timing, frequency, and magnitude of these applied fields to efficiently transform parahydrogen spin order into heteronuclear magnetization in the strong coupling regime of protons is nontrivial though, and earlier sequences for application to this field regime have been either been geared towards specific coupling patterns, or have required piecewise or recursive application for optimal results. See, Goldman, M.; Johannesson, H.; Axelsson, O.; Karlsson, M. *Magn Reson Imaging* 2005, 23, 153-7; and Kadlecek, S.; Emami, K.; Ishii, M.; Rizi, R. *J Magn Reson* 2011, 205, 9-13, each of which is incorporated herein in its entirety by reference.

Accordingly, a need exists for a single, non-recursive pulse sequence for transferring nuclear singlet state spin order into heteronuclear magnetization localized on a heteronucleus at low magnetic field in the strong coupling regime of protons.

In terms of existing theory, pulsed methods for efficiently converting parahydrogen spin order into net heteronuclear magnetization at low magnetic fields are limited to systems that have only three NMR active nuclei. See, Goldman, M.; Johannesson, H.; Axelsson, O.; Karlsson, M. *Magn Reson Imaging* 2005, 23, 153-7; and Kadlecek, S.; Emami, K.; Ishii, M.; Rizi, R. *J Magn Reson* 2011, 205, 9-13, each of which is incorporated herein in its entirety by reference. While raw singlet-states can be long lived and useful in some applications without further manipulation, when applied to biomedicine it is useful to convert these states into net magnetization on a long-lived heteronucleus for storage and to allow subsequent detection using standard imaging techniques. Transforming these states into longitudinal heteronuclear magnetization also maximizes spectral dispersion during subsequent imaging experiments and reduces interference from the intense proton background arising from water in vivo. Furthermore, the initial singlet-state of an AA'XY spin system will generally evolve unless $J_{1X}-J_{1Y}-J_{2X}+J_{2Y}=0$ and $J_{1X}+J_{1Y}-J_{2X}-J_{2Y}=0$. Locking magnetization on a heteronucleus therefore makes it unnecessary to synchronize detection with accrued evolution of the initial singlet-state.

Accordingly, a need exists for a single, non-recursive pulse sequence for transferring nuclear singlet state spin order into heteronuclear magnetization localized on a heteronucleus for a system having at least four NMR active nuclei.

SUMMARY

This disclosure provides methods of performing Nuclear Magnetic Resonance (NMR) spectroscopy or Magnetic Resonance Imaging (MRI). The methods may include: a) generating a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$; b) transferring the nuclear singlet state spin order into heteronuclear magnetization localized on S by applying a single, non-recursive pulse sequence at a low magnetic field in the strong coupling regime of protons; and c) performing NMR spectroscopy or MRI with the compound comprising heteronuclear magnetization localized on S. The $|J_{1S}-J_{2S}|$ may be non-zero. The pulse sequence may include a plurality of sequential radio frequency pulses separated by independent evolution interval. The pulse sequence may be capable of transferring at least about 75% of the nuclear singlet state spin order into heteronuclear magnetization localized on S at any $|J_{1S}-J_{2S}|$ when the independent evolution intervals are optimized.

This disclosure also provides methods including: a) generating a compound comprising a first nuclear species ($I_1$), a second nuclear species ($I_2$), a third nuclear species (S), a fourth nuclear species (R) and a nuclear singlet state spin order localized on $I_1$ and $I_2$; b) transferring the nuclear singlet state spin order into heteronuclear magnetization localized on S by applying a pulse sequence at a low magnetic field in the strong coupling regime of protons; and c) performing NMR spectroscopy or MRI with the compound comprising heteronuclear magnetization localized on S.

This disclosure also provides methods including: a) determining J-couplings for a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$; b) calculating optimal evolution intervals for a single, non-recursive pulse sequence at low magnetic field in the strong coupling regime of protons using the J-couplings, the pulse sequence comprising a sequential plurality of radio frequency pulses separated by independent evolution intervals; c) generating the compound; d) transferring the nuclear singlet state spin order into heteronuclear magnetization localized on S by applying the pulse sequence with optimal evolution intervals to the compound; and e) performing NMR spectroscopy or MRI with the compound comprising heteronuclear magnetization localized on S. The pulse sequence may transfer at least about 75% of the nuclear singlet state spin order into heteronuclear magnetization localized on S at any $|J_{1S}-J_{2S}|$.

This disclosure also provides NMR spectroscopy and MRI systems configured to perform the methods described herein.

DETAILED DESCRIPTION

Figure 1:
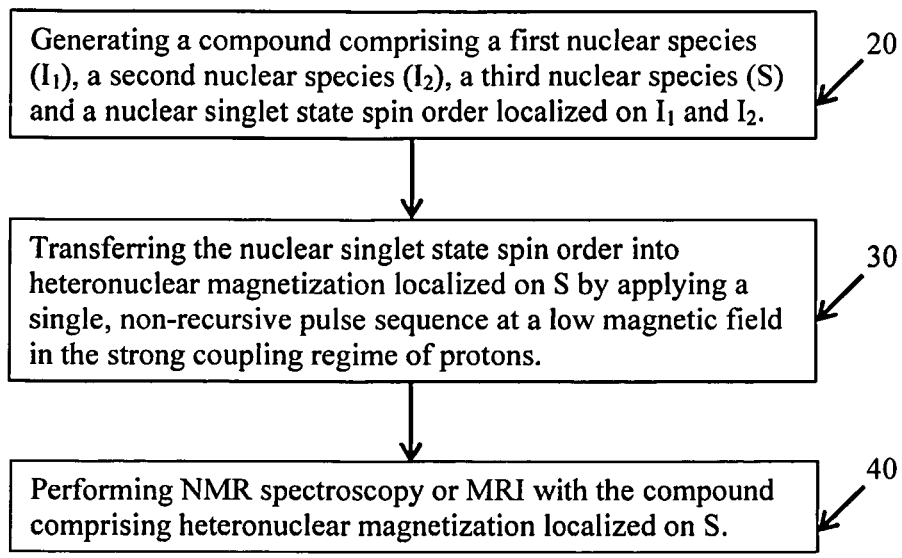
FIG. 1 is a flow chart illustrating methods of performing Nuclear Magnetic Resonance spectroscopy or Magnetic Resonance Imaging (MRI) in accordance with an embodiment of this disclosure.

The methods and systems disclosed herein are not limited in their applications to the details of construction and the arrangement of components described herein. The methods and apparatuses are capable of other embodiments and of being practiced or of being carried out in various ways. Also it is to be understood that the phraseology and terminology used herein is for the purpose of description only, and should not be regarded as limiting. Ordinal indicators, such as first, second, and third, as used in the description and the claims to refer to various structures, are not meant to be construed to indicate any specific structures, or any particular order or configuration to such structures. All methods described herein can be performed in any suitable order unless otherwise indicated herein or otherwise clearly contradicted by context. The use of any and all examples, or exemplary language (e.g., "such as") provided herein, is intended merely to better illuminate the methods and apparatuses disclosed herein and does not pose a limitation on the scope of the methods and apparatuses unless otherwise claimed. No language in the specification, and no structures shown in the drawings, should be construed as indicating that any non-claimed element is essential to the practice of the methods and apparatuses disclosed herein.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration, volume or the like range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein.

This disclosure provides methods of performing Nuclear Magnetic Resonance (NMR) spectroscopy or Magnetic Resonance Imaging (MRI). This disclosure also provides systems configured to execute the methods of performing NMR spectroscopy or MRI.

I. Methods

Referring to FIG. 1, this disclosure provides a method of performing NMR spectroscopy or MRI spectroscopy. The method may comprise: a) generating a compound comprising a first nuclear species ($I_1$), a second nuclear species ($I_2$), a third nuclear species (S) and a nuclear singlet state spin order localized on $I_1$ and $I_2$ 20; b) transferring the nuclear singlet state spin order into heteronuclear magnetization localized on S by applying a single, non-recursive pulse sequence at a low magnetic field in the strong coupling regime of protons 30; and c) performing NMR spectroscopy or MRI with the compound comprising heteronuclear magnetization localized on S 40.

The compound may comprise a heteronuclear coupling asymmetry ($|J_{1S}-J_{2S}|$). In certain embodiments, $|J_{1S}-J_{2S}|$ may be non-zero.

A. Generating a Compound Comprising a Nuclear Singlet State Spin Order

The method may comprise generating a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$. The method may comprise generating a compound comprising a first nuclear species ($I_1$), a second nuclear species ($I_2$), a third nuclear species (S), a fourth nuclear species (R) and a nuclear singlet state spin order localized on $I_1$ and $I_2$.

Generating a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$ may be executed by any known method of creating a nuclear singlet state spin order. Generating a compound comprising a first nuclear species ($I_1$), a second nuclear species ($I_2$), a third nuclear species (S), a fourth nuclear species (R) and a nuclear singlet state spin order localized on $I_1$ and $I_2$ may be executed by any known method of creating a nuclear singlet state spin order. Generating a compound comprising a nuclear singlet state spin order may comprise hyperpolarizing the compound by parahydrogen induced polarization (PHIP), any method of forming a generic singlet state other than protons capable of endowing its spin order onto another molecule, singlet states formed by running the pulse sequences disclosed herein in reverse, and combinations thereof. Examples of suitable methods include, but are not limited to, those disclosed in U.S. Pat. Nos. 6,574,495 and 6,872,380, each of which is incorporated herein in its entirety by reference.

The compound may be hyperpolarized.

Nuclear species may be any NMR-active nuclei capable of exhibiting the spin order and magnetization properties described herein. Examples of nuclear species include, but are not limited to $^1H$, $^{13}C$, $^{15}N$, $^{31}P$, $^{19}F$, $^{29}Si$, and $^{103}Rh$. Nuclear species may be suited to hyperpolarization. Nuclear species may be suited to parahydrogen induced polarization (PHIP).

Compounds may have naturally occurring amounts of nuclear species or may be enriched to contain more nuclear species than naturally occurring compounds.

The heteronuclear coupling asymmetry ($|J_{1S}-J_{2S}|$) may be non-zero. Without wishing to be bound by theory, in the limit that the heteronuclear coupling asymmetry approaches zero, the overall pulse sequence duration required for optimal magnetization transfer approaches infinity.

B. Transferring the Nuclear Singlet State Spin Order into Heteronuclear Magnetization The method may comprise transferring the nuclear singlet state spin order into heteronuclear magnetization localized on S by applying a single, non-recursive pulse sequence at a low magnetic field in the strong coupling regime of protons.

As used herein, low magnetic field includes a magnetic field that is non-zero and less than about 100 mT.

The pulse sequences 100, 200 disclosed herein may comprise a sequential plurality of radio frequency pulses 110, 111, 112, 113, 210, 211, 212, 213, 214, 215 separated by independent evolution intervals 120, 121, 122, 123, 220, 221, 222, 223, 224, 225. The pulse sequences may comprise at least 4 sequential radio frequency pulses or at least 6 sequential radio frequency pulses. The pulse sequences may comprise 4, 6, 8, 10, 12, 14, 16, 18, 20 or more sequential radio frequency pulses. Higher numbers of radio frequency pulses provide greater numbers of independent evolution intervals, thereby allowing higher order spin systems to be optimized.

The pulse sequence may comprise a first portion 130, 230 and a second portion 131, 231. The first portion may convert the nuclear singlet state spin order localized on $I_1$ and $I_2$ into a pure state which is coupled to S. The second portion may convert the pure state which is coupled to S into longitudinal net magnetization on S. The first and second portion may contain equal or unequal numbers of radio frequency pulses or evolution intervals.

The duration of the pulse sequence may equal the sum of the independent evolution intervals.

The pulse sequences may further comprise applying focusing pulses between the sequential radio frequency pulses. A non-limiting example of applying focusing pulses between the sequential radio frequency pulses includes applying focusing pulses at ¼ and ¾ of each independent evolution interval.

The pulse sequences disclosed herein is configured to transfer at least about 75%, at least about 80%, at least about 85%, at least about 90%, at least about 95%, at least about 96%, at least about 97%, at least about 98%, at least about 99% or about 100% of the nuclear singlet state spin order into heteronuclear magnetization localized on S at any $|J_{1S}-J_{2S}|$ when the independent evolution intervals are optimized.

The pulse sequences may be optimized in accordance with techniques known to those skilled in the relevant art. The pulse sequences may be optimized with techniques described herein. The pulse sequences may be optimized by calculating optimal evolution intervals as described herein. It should be recognized that pulse sequence optimization typically proceeds without adding, removing, reordering or altering the radio frequency pulses.

Figure 2:
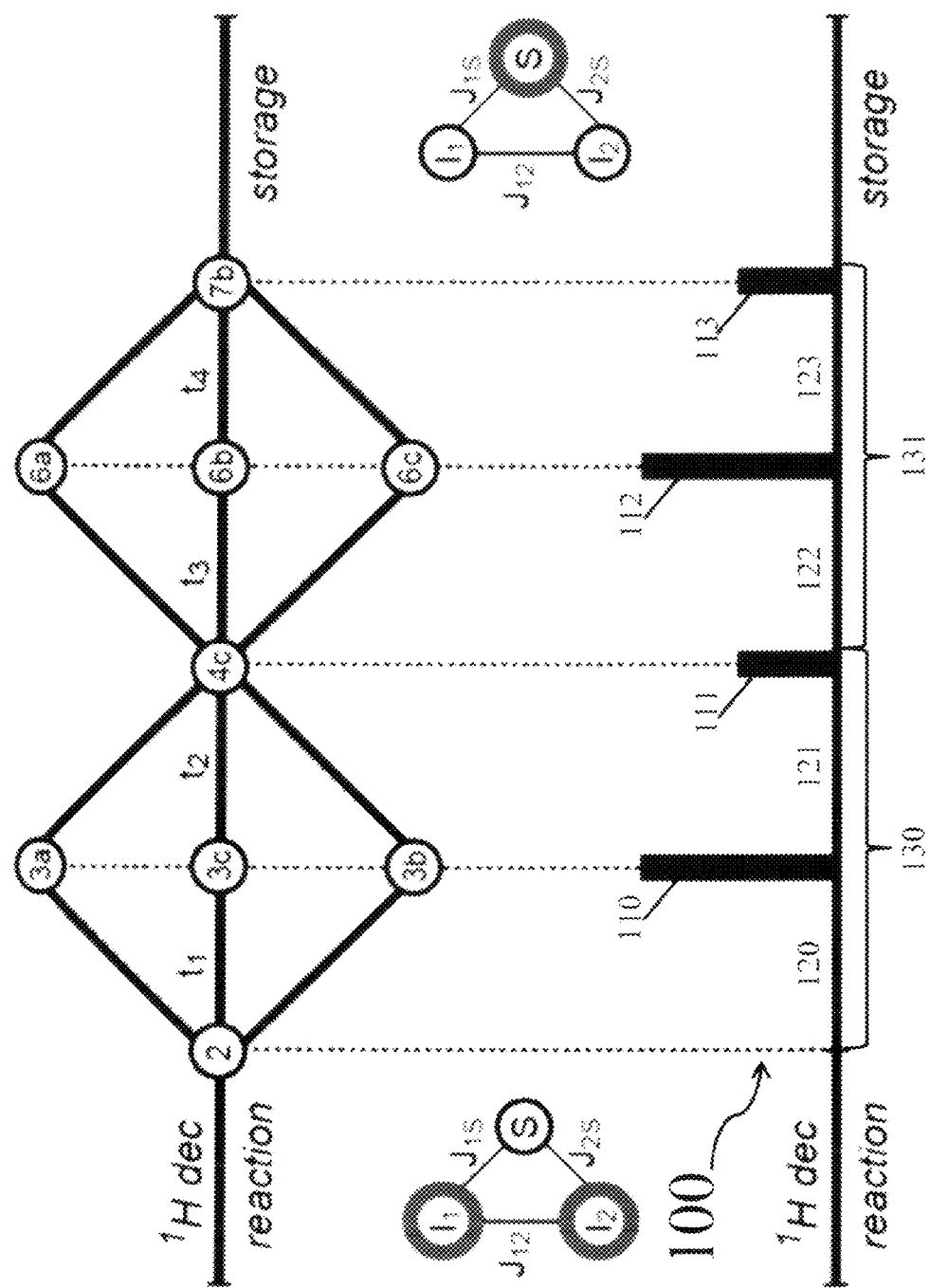
FIG. 2 is a schematic representation of the evolution of density matrix components (top) corresponding to a hyper-SHIELDED pulse sequence (bottom).

Referring to FIG. 2, the pulse sequences 100 disclosed herein may comprise the following sequential elements: a) a time $t_1$ after generating the compound 120; b) a 180(+x) pulse on $I_1$ and $I_2$ 110; c) a time $t_2$ 121; d) a 90(+y) pulse on S 111; e) a time $t_3$ 122; f) a 180(+x) pulse on $I_1$ and $I_2$ 112; g) a time $t_4$ 123; and h) a 90(+x) pulse on S 113. Referring to FIG. 2, the pulse sequences 100 disclosed herein may comprise the following sequential steps: a) waiting a time $t_1$ after generating the compound 120; b) applying a 180(+x) pulse on $I_1$ and $I_2$ 110; c) waiting a time $t_2$ 121; d) applying a 90(+y) pulse on S 111; e) waiting a time $t_3$ 122; f) applying a 180(+x) pulse on $I_1$ and $I_2$ 112; g) waiting a time $t_4$ 123; and h) applying a 90(+x) pulse on S 113. In certain embodiments, $t_1$, $t_2$, $t_3$ and $t_4$ may be selected to maximize transfer of the nuclear singlet state spin order localized on $I_1$ and $I_2$ into longitudinal net magnetization on S. In certain embodiments, $t_1$ and $t_2$ may be selected to maximize transfer of the nuclear singlet state spin order localized on $I_1$ and $I_2$ into a pure state which is coupled to S, $t_3$ and $t_4$ may be selected to maximize transfer of the pure state which is coupled to S into longitudinal net magnetization on S, or a combination thereof. Referring to FIG. 2, the pulse sequence 100 may comprise a first portion 130 and second portion 131. The first portion may include steps a)-d). The second portion may include steps e)-h).

Figure 8:
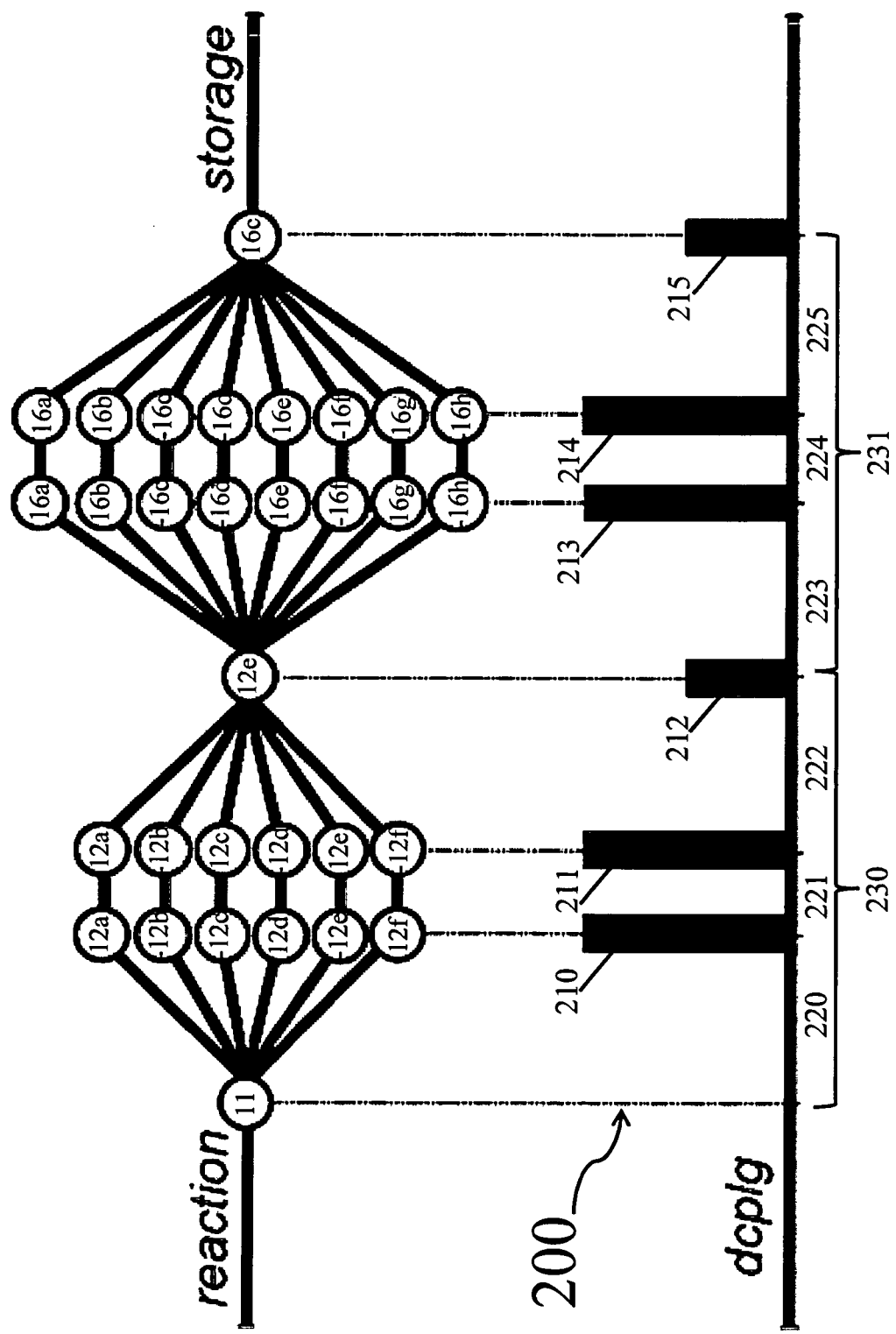
FIG. 8 is a schematic representation of the evolution of density matrix components (top) corresponding to a hyper-SHIELDED-4 pulse sequence (bottom).

Referring to FIG. 8, the pulse sequences 200 disclosed herein may comprise the following sequential elements: a) a time $t_1$ after generating the compound 220; b) a 180(+x) pulse on S 210; c) a time $t_2$ 221; d) a 180(+x) pulse on $I_1$ and $I_2$ 211; e) a time $t_3$ 222; f) a 90(+y) pulse on S 212; g) a time $t_4$ 223; h) a 180(+x) pulse on S 213; i) a time $t_5$ 224; j) a 180(+x) pulse on $I_1$ and $I_2$ 214; k) a time $t_6$ 225; and l) a 90(+x) pulse on S 215. Referring to FIG. 8, the pulse sequences 200 disclosed herein may comprise the following sequential steps: a) waiting a time $t_1$ after generating the compound 220; b) applying a 180(+x) pulse on S 210; c) waiting a time $t_2$ 221; d) applying a 180(+x) pulse on $I_1$ and $I_2$ 211; e) waiting a time $t_3$ 222; f) applying a 90(+y) pulse on S 212; g) waiting a time $t_4$ 223; h) applying a 180(+x) pulse on S 213; i) waiting a time $t_5$ 224; j) applying a 180(+x) pulse on $I_1$ and $I_2$ 214; k) waiting a time $t_6$ 225; and l) applying a 90(+x) pulse on S 215. In certain embodiments, $t_1$, $t_2$, $t_3$, $t_4$, $t_5$ and $t_6$ may be selected to maximize transfer of the nuclear singlet state spin order localized on $I_1$ and $I_2$ into longitudinal net magnetization on S. In certain embodiments, $t_1$, $t_2$ and $t_3$ may be selected to maximize transfer of the nuclear singlet state spin order localized on and $I_2$ into a pure state which is coupled to S, $t_4$, $t_5$ and $t_6$ may be selected to maximize transfer of the pure state which is coupled to S into longitudinal net magnetization on S, or a combination thereof. Referring to FIG. 8, the pulse sequence 200 may comprise a first portion 230 and second portion 231. The first portion may include steps a)-f). The second portion may include steps g)-l).

The pulse sequence may be preceded by a decoupling sequence. The decoupling sequence may be a sequence for decoupling $I_1$ and $I_2$, a proton decoupling sequence, or a combination thereof.

1. Hyper-SHIELDED Pulse Sequence

In some embodiments, the pulse sequence may comprise a hyper-SHIELDED pulse sequence. The theory behind the hyper-SHIELDED pulse sequence for a three spin system is as follows.

The Hamiltonian of the three spin system (AA'X=$I_1 I_2 S$) formed from the parahydrogen addition product (PASADENA, see, Bowers, C. R.; Weitekamp, D. P. *Physical Review Letters* 1986, 57, 2645-2648; and Bowers, C. R.; Weitekamp, D. P. *Journal of the American Chemical Society* 1987, 109, 5541-5542, each of which is incorporated herein in its entirety by reference) and a coupled heteronucleus in the strong proton coupling regime can be written as:

$$H = 2\pi[J_{12}(I_1 \cdot I_2) + J_{1S} I_{1z} S_z + J_{2S} I_{2z} S_z]. \tag{1}$$

The initial density matrix of parahydrogen at low field in the strong coupling regime of protons can be written:

$$\sigma_0 = \tfrac{1}{4} - I_1 \cdot I_2. \tag{2}$$

The $I_{1z} I_{2z}$ component of this initial density matrix commutes with all components, and hence does not evolve under the Hamiltonian in Eq. 1. The remainder of the initial density matrix in the PASADENA addition product evolves during the interval $t_1$ under the influence of the Hamiltonian according to the following expression:

$$\sigma_1 \overset{t_1}{\to} [\sin^2\theta + (\cos^2\theta)\cos(2\pi\Omega t_1)](I_{1x} I_{2x} + I_{1y} I_{2y}) \tag{3a}$$

$$+ (\cos\theta)\sin(2\pi\Omega t_1) 2(I_{1y} I_{2x} - I_{1x} I_{2y}) S_z \tag{3b}$$

$$+ (\sin\theta)(\cos\theta)[1 - \cos(2\pi\Omega t_1)](I_{1z} - I_{2z}) S_z \tag{3c}$$

where $$\cos\theta = \frac{\Delta}{\sqrt{1+\Delta^2}},$$

$$\sin\theta = \frac{\Delta}{\sqrt{1+\Delta^2}},$$

$$\Delta = [J_{1S} - J_{2S}](2 \cdot J_{12})^{-1},$$

and $$\Omega = J_{12}(1+\Delta^2)^{\tfrac{1}{2}}.$$

After applying a 180(+x) pulse on protons, the density operator $\sigma_2$ evolves according to:

$$\sigma_2 \overset{t_2}{\to} \left[ -\cos 2\theta (\sin^2\theta) + \tfrac{1}{2}\sin^2 2\theta (\cos(2\pi\Omega t_1) + \cos(2\pi\Omega t_2)) + \right. \tag{4a}$$

$$\left. \cos 2\theta (\cos^2\theta)\cos(2\pi\Omega t_1)\cos(2\pi\Omega t_2) \right] +$$

$$(\cos^2\theta)\sin(2\pi\Omega t_1)\sin(2\pi\Omega t_2) \Big| (I_{1x} I_{2x} + I_{1y} I_{2y})$$

$$+ [\sin(2\theta)\sin(\theta)\sin(2\pi\Omega t_2) + \cos(2\theta)\cos(\theta)(2\pi\Omega t_1)\sin(2\pi\Omega t_2) - \tag{4b}$$

$$\cos(\theta)\sin(2\pi\Omega t_1)\cos(2\pi\Omega t_2)] 2(I_{1y} I_{2x} - I_{1x} I_{2y}) S_z$$

$$+ \left[ -\tfrac{1}{2}\sin(2\theta) \right. \tag{4c}$$

$$(\cos(2\theta) + 2\sin^2(\theta) - 2\cos^2(\theta)\cos(2\pi\Omega t_1) + \cos(2\theta)\cos(2\pi\Omega t_1)$$

$$\left. \cos(2\pi\Omega t_2) + \sin(2\pi\Omega t_1)\sin(2\pi\Omega t_2)) \right] (I_{1z} - I_{2z}) S_z$$

In order to drive the terms in Eq. 4 exclusively to Eq. 4c, the intervals $t_1$ and $t_2$ are chosen to satisfy Equations 5a and 5b:

$$-\cos 2\theta \sin^2\theta + \frac{1}{2}\sin^2 2\theta(\cos(2\pi\Omega t_1) + \cos(2\pi\Omega t_2)) + \quad (5a)$$
$$\cos(2\theta)\cos^2\theta\cos(2\pi\Omega t_1)\cos(2\pi\Omega t_2) +$$
$$\cos^2\theta\sin(2\pi\Omega t_1)\sin(2\pi\Omega t_2) = 0,$$

$$\sin(2\theta)\sin(\theta)\sin(2\pi\Omega t_2) + \cos(2\theta)\cos(\theta)\cos(2\pi\Omega t_1)\sin(2\pi\Omega t_2) - \quad (5b)$$
$$\cos(\theta)\sin(2\pi\Omega t_1)\cos(2\pi\Omega t_2) = 0$$

A 90(+y) pulse on the S spin then converts the state $(I_{1z}-I_{2z})S_z$ into $(I_{1z}-I_{2z})S_x$. During the subsequent interval $t_3$, this state evolves into three terms:

$$\sigma_3 = (I_{1z} - I_{2z})S_x \xrightarrow{t_3} \cos(2\pi\Omega t_3)(I_{1z} - I_{2z})S_x \quad (6a)$$

$$+\cos(\theta)\sin(2\pi\Omega t_3)\frac{1}{2}S_y(I - 4I_{1z}I_{2z}) \quad (6b)$$

$$-\sin(\theta)\sin(2\pi\Omega t_3)2(I_{1y}I_{2x} - I_{1x}I_{2y})S_x \quad (6c)$$

A proton 180(+x) pulse is then applied, and during the subsequent interval $t_4$, the density matrix evolves according to the expression:

$$\sigma_4 \xrightarrow{t_4} [ \quad (7a)$$
$$\cos(2\pi\Omega t_3)\cos(2\pi\Omega t_4) + \cos(2\theta)\sin(2\pi\Omega t_3)\sin(2\pi\Omega t_4)](I_{1z} - I_{2z})S_x$$

$$+[\cos(\theta)\cos(2\pi\Omega t_3)\sin(2\pi\Omega t_4) - \sin(2\theta)\sin(\theta)\sin(2\pi\Omega t_3) - \quad (7b)$$
$$\cos(\theta)\cos(2\theta)\sin(2\pi\Omega t_3)\cos(2\pi\Omega t_4)]\frac{1}{2}S_y(I - 4I_{1z}I_{2z})$$

$$+[\sin(\theta)\cos(2\theta)\sin(2\pi\Omega t_3)\cos(2\pi\Omega t_4) - \sin(\theta)\cos(2\pi\Omega t_3)\sin(2\pi\Omega t_4) - \quad (7c)$$
$$\sin(2\theta)\cos(\theta)\sin(2\pi\Omega t_3)]2(I_{1y}I_{2x} - I_{1x}I_{2y})S_x$$

The intervals $t_3$ and $t_4$ are chosen to satisfy the following set of equations:

$$\cos(2\pi\Omega t_3)\cos(2\pi\Omega t_4) + \cos(2\theta)\sin(2\pi\Omega t_3)\sin(2\pi\Omega t_4) = 0 \quad (8a)$$

$$\sin(\theta)\cos(2\theta)\sin(2\pi\Omega t_3)\cos(2\pi\Omega t_4) - \quad (8b)$$
$$\sin(\theta)\cos(2\pi\Omega t_3)\sin(2\pi\Omega t_4) - \sin(2\theta)\cos(\theta)\sin(2\pi\Omega t_3) = 0$$

This condition is satisfied when:

$$\tan(2\pi\Omega t_3) = -1/\sqrt{1+2\cos(2\theta)} \quad (9a)$$

$$\tan(2\pi\Omega t_4) = 1/\sqrt{1+2\cos(3\theta)} \quad (9b)$$

Finally, a 90(+x) pulse converts the term from Eq. 7b into longitudinal magnetization on the heteronucleus for storage until subsequent detection in vivo. The pulse sequence diagram (bottom) and schematic of spin evolution represented by equations 2-7 (top) is illustrated in FIG. 2. The numbers in the schematic of spin evolution correspond to equation numbers for the density matrices set forth above.

2. Hyper-SHIELDED-4 Pulse Sequence

In some embodiments, the pulse sequence may comprise a hyper-SHIELDED-4 (hS4) pulse sequence. The theory behind the hyper-SHIELDED-4 pulse sequence for a four spin system is as follows.

The Hamiltonian of the four spin system formed by the addition of parahydrogen to a molecule containing two heteronuclei can be written as:

$$H = 2\pi[J_{12}(I_{1x}I_{2x} + I_{1y}I_{2y} + I_{1z}I_{2z}) + J_{1S}I_{1z}S_z + \quad (10)$$
$$J_{1R}I_{1z}R_z + J_{2S}I_{2z}S_z + J_{2R}I_{2z}R_z + J_{SR}S_zR_z].$$

In this expression, $I_1$ and $I_2$ refer to protons while S and R refer to heteronuclei which are weakly coupled to one another and to the protons. The initial density matrix of parahydrogen can be written in the strong coupling regime of protons as:

$$\sigma_1 = \frac{1}{4} - (I_{1x}I_{2x} + I_{1y}I_{2y} + I_{1z}I_{2z}) \quad (11)$$

The $I_{1z}I_{2z}$ term component of this initial density matrix commutes with Hamiltonian given in Equation 1. The remainder of the initial density matrix evolves with hyper-SHIELDED-4 (hS4, FIG. 8) during the interval $t_1$ under the influence of the Hamiltonian according to the following expression:

$$\sigma_1(t_1) = \frac{1}{2}[\sin^2\theta_1 + \cos\theta_1\cos(2\pi\Omega_1 t_1) + \sin^2\theta_2 + \cos\theta_2\cos(2\pi\Omega_2 t_2)] \quad (12a)$$
$$(I_{1x}I_{2x} + I_{1y}I_{2y})$$

$$+ \frac{1}{2}[\sin^2\theta_1 + \cos\theta_1\cos(2\pi\Omega_1 t_1) - \sin^2\theta_2 - \cos\theta_2\cos(2\pi\Omega_2 t_2)] \quad (12b)$$
$$4(I_{1x}I_{2x} + I_{1y}I_{2y})S_zR_z$$

$$+ \frac{1}{2}[\cos\theta_1\sin(2\pi\Omega_1 t_1) - \cos\theta_2\sin(2\pi\Omega_2 t_2)]2(I_{1y}I_{2x} + I_{1x}I_{2y})S_z \quad (12c)$$

$$+ \frac{1}{2}[\cos\theta_1\sin(2\pi\Omega_1 t_1) - \cos\theta_2\sin(2\pi\Omega_2 t_2)]2(I_{1y}I_{2x} + I_{1x}I_{2y})R_z \quad (12d)$$

$$+ \frac{1}{4}[\sin 2\theta_1(1 - \cos(2\pi\Omega_1 t_1)) - \sin 2\theta_2(1 - \cos(2\pi\Omega_2 t_2))](I_{1z} - I_{1z})S_z \quad (12e)$$

$$+ \frac{1}{4}[\sin 2\theta_1(1 - \cos(2\pi\Omega_1 t_1)) - \sin 2\theta_2(1 - \cos(2\pi\Omega_2 t_2))](I_{1z} - I_{1z})R_z \quad (12f)$$

where $$\Omega_1 = J_{12}\sqrt{1+\Delta_1^2} \quad (13)$$
$$\Omega_2 = J_{12}\sqrt{1+\Delta_2^2}$$
$$\sin\theta_1 = \frac{1}{\sqrt{1+\Delta_1^2}}$$
$$\sin\theta_2 = \frac{1}{\sqrt{1+\Delta_2^2}}$$
$$\cos\theta_1 = \frac{\Delta}{\sqrt{1+\Delta_1^2}}$$
$$\cos\theta_2 = \frac{\Delta}{\sqrt{1+\Delta_2^2}}$$
$$\Delta_1 = \frac{J_{1S} + J_{1R} - J_{2S} - J_{2R}}{2J_{12}}$$
$$\Delta_2 = \frac{J_{1S} - J_{1R} - J_{2S} + J_{2R}}{2J_{12}}$$

The first half of hS4 ($t_1$, $t_2$, $t_3$) converts the initial singlet-state to a pure 12e state which is coupled to heteronucleus S. The density matrix following propagation through $t_1$, $t_2$, $t_3$ can be written as:

$$\sigma_N(t_1,t_2,t_3) = e^{-iHt_3}[R_X^I(\pi)]^{-1}e^{-iHt_2}[R_X^S(\pi)]^{-1}\cdot$$
$$e^{-iHt_1}\sigma_0 e^{iHt_1}R_X^I(\pi)e^{iHt_2}R_X^I(\pi)e^{iHt_3} \quad (14)$$

Evolution delays $t_1$, $t_2$, and $t_3$ are then adjusted to minimize the difference between the $\sigma_N$ and 12e according to the following equation:

$$\min[\sigma_N(t_1,t_2,t_3) - 12e] \quad (15)$$

A 90(+y) pulse on the S spin then converts the state 12e $(I_{1z}-I_{2z})S_z$ into $(I_{1z}-I_{2z})S_x$. During the subsequent interval $t_4$, this state then evolves into eight terms:

$$\sigma_N(t_4) = \cos(\pi J_{SR}t_4)[\cos(\pi\Omega_1 t_4)\cos(\pi\Omega_2 t_4) - \qquad (16a)$$
$$\cos(\theta_1-\theta_2)\sin(\pi\Omega_1 t_4)\sin(\pi\Omega_2 t_4)]S_x(I_{1z}-I_{2z})$$

$$-\sin(\pi J_{SR}t_4)[\cos\theta_1\sin(\pi\Omega_1 t_4)\cos(\pi\Omega_2 t_4) + \qquad (16b)$$
$$\cos\theta_2\cos(\pi\Omega_1 t_4)\sin(\pi\Omega_2 t_4)]S_x(I-4I_{1z}I_{2z})R_z$$

$$+\cos(\pi J_{SR}t_4)[\cos\theta_1\sin(\pi\Omega_1 t_4)\cos(\pi\Omega_2 t_4) + \qquad (16c)$$
$$\cos\theta_2\cos(\pi\Omega_1 t_4)\sin(\pi\Omega_2 t_4)]\tfrac{1}{2}S_y(I-4I_{1z}I_{2z})$$

$$+\cos(\pi J_{SR}t_4)[\cos\theta_1\sin(\pi\Omega_1 t_4)\cos(\pi\Omega_2 t_4) - \qquad (16d)$$
$$\cos(\theta_1-\theta_2)\sin(\pi\Omega_1 t_4)\sin(\pi\Omega_2 t_4)]2S_y(I_{1z}-I_{2z})R_z$$

$$-\cos(\pi J_{SR}t_4)[\sin(\theta_1-\theta_2)\sin(\pi\Omega_1 t_4)\sin(\pi\Omega_2 t_4)]\cdot 4 \qquad (16e)$$
$$S_y(I_{1y}I_{2x}-I_{1x}I_{2y})R_z$$

$$-\sin(\pi J_{SR}t_4)[\sin\theta_1\sin(\pi\Omega_1 t_4)\cos(\pi\Omega_2 t_4) + \qquad (16f)$$
$$\sin\theta_2\cos(\pi\Omega_1 t_4)\sin(\pi\Omega_2 t_4)]4S_y(I_{1y}I_{2x}-I_{1x}I_{2y})R_z$$

$$-\cos(\pi J_{SR}t_4)[\sin\theta_1\sin(\pi\Omega_1 t_4)\cos(\pi\Omega_2 t_4) + \qquad (16g)$$
$$\sin\theta_2\cos(\pi\Omega_1 t_4)\sin(\pi\Omega_2 t_4)]2S_x(I_{1y}I_{2x}+I_{1x}I_{2y})$$

$$-\sin(\pi J_{SR}t_4)[\sin(\theta_1-\theta_2)\sin(\pi\Omega_1 t_4)\sin(\pi\Omega_2 t_4)]\cdot 2S_y(I_{1y}I_{2x}+I_{1x}I_{2y}) \qquad (16h)$$

Since the $I_{1z}I_{2z}$ term does not evolve with time, the second phase of hS4 transforms $\sigma_N$ into a pure single quantum S-coherence (term 16c).

A 180(+x) pulse on the S channel is applied following evolution delay $t_4$. A 180(+x) pulse on the proton channel is then applied following the $t_5$ interval. The density matrix then evolves during the $t_6$ evolution delay to the targeted final state:

$$\sigma_F(t_4,t_5,t_6) = e^{-iHt_6}[R_X^I(\pi)]^{-1}e^{-iHt_5}[R_X^S(\pi)]^{-1}\cdot$$
$$e^{-iHt_4}\sigma_{int}e^{iHt_4}R_X^S(\pi)e^{iHt_5}R_X^I(\pi)e^{iHt_6} \qquad (17)$$

The time intervals ($t_4$, $t_5$, and $t_6$) are adjusted to minimize the difference between the up and the desired pure 16c term:

$$\min[\sigma_N(t_1,t_2,t_3)-16c] \qquad (18)$$

Finally, a 90(+x) pulse converts the 16c term into longitudinal net magnetization on the heteronucleus S for storage until subsequent detection.

It should be appreciated that the phases discloses herein can be incremented sequentially by an arbitrary amount to achieve similar effect. For example, if all pulses received a phase increment of delta(phi), the effect of the pulse sequence would be similar.

C. Determining J-Couplings

J-couplings can be determined in accordance with techniques known to those skilled in the relevant arts. The method may comprise determining J-couplings for a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$.

Determining J-couplings for a compound may comprise experimentally determining J-couplings, theoretically calculating J-couplings and combinations thereof. Examples of experimentally determining J-couplings include, but are not limited to, measuring first order couplings at high field, HSQC, HMQC, COSY, or multidimensional acquisitions that allow scalar evolution to be detected indirectly, and combinations thereof. Examples of theoretically calculating J-couplings include, but are not limited to, density functional theory calculations, ab initio calculations, and combinations thereof. Determining J-couplings for a compound may comprise calculations involving equations 1-18.

D. Calculating Optimal Evolution Intervals

Calculating optimal evolution intervals can be performed in accordance with techniques known to those skilled in the relevant arts. The method may comprise calculating optimal evolution intervals for a single, non-recursive pulse sequence at low magnetic field in the strong coupling regime of protons. The method may comprise calculating optimal evolution intervals using the J-couplings determined in the determining J-couplings for a compound step.

Calculating optimal evolution intervals may comprise inverting a density matrix expression representing the evolution of spin states of the compound during application the pulse sequence to the compound, minimizing the difference between a density matrix expression representing the evolution of spin states of the compound during application of the pulse sequence and a desired state which is coupled to S, or a combination thereof.

Calculating optimal evolution intervals may comprise use of a computer code for minimizing the difference between a density matrix expression representing the evolution of a compound during applying the pulse sequence and a desired state which is couple to S. Examples of a computer code for this purpose include, but are not limited to, the hyper-SHIELDED minimization code and the hyper-SHIELDED-4 minimization code described herein. The hyper-SHIELDED minimization code is set forth below. The hyper-SHIELDED-4 minimization code is set forth in the computer program listing appendix in a file entitled file entitled "function_tau-_hs4.txt".

E. Performing NMR Spectroscopy or MRI

Performing NMR spectroscopy or MRI can be executed in accordance with techniques known to those skilled in the relevant arts. Examples of performing NMR spectroscopy or MRI include, but are not limited to, collecting, processing, storing and/or displaying NMR spectroscopy data in accordance with techniques known to those skilled in the relevant arts, infusing the compound in vivo for MRI in accordance with techniques known to those skilled in the relevant arts, and combinations thereof.

II. Systems

This disclosure provides NMR spectroscopy or MRI systems configured to execute the methods disclosed herein. Suitable NMR spectroscopy or MRI systems are known to those skilled in the relevant arts and capable of being configured to execute the methods disclosed herein. NMR spectroscopy or MRI systems may be configured to deliver the pulse sequences disclosed herein. For example, NMR spectroscopy or MRI systems may be pre-configured using software to deliver the pulse sequences disclosed herein.

EXAMPLES

The following examples are presented to illustrate the present invention and to assist one of ordinary skill in making and using the same. The examples are not intended in any way to otherwise limit the scope of the invention.

Example 1

Hyper-SHIELDED Pulse Sequence

Approximately 98% parahydrogen gas was synthesized by pulsing ambient research grade hydrogen gas at 14 bar (200 psi) into a catalyst-filled (iron oxide) copper chamber held at 14 K using a previously described semi-automated parahydrogen generator. See, Feng, B. B.; Coffey, A. M.; Colon, R. D.; Chekmenev, E. Y.; Waddell, K. W. *Journal of Magnetic Resonance* 2012, 214, 258-262, which is incorporated herein in its entirety by reference. Fresh batches of parahydrogen were collected in 10 L aluminum storage tanks (14745-SHF-GNOS, Holley, Ky., USA), used without Teflon lining or additional modification.

The preparation of PASADENA (see, Bowers, C. R.; Weitekamp, D. P. *Physical Review Letters* 1986, 57, 2645-2648; and Bowers, C. R.; Weitekamp, D. P. *Journal of the American Chemical Society* 1987, 109, 5541-5542, each of which is incorporated herein in its entirety by reference) precursor molecules was similar to those previously described (see, Waddell, K. W.; Coffey, A. M.; Chekmenev, E. Y. *J. Am. Chem.* 2011, 133, 97-101) with the exception that water was used in place of 99.8% $D_2O$ as a solvent. Briefly, 1,4-bis-(phenyl-3-propane sulfonate)phosphine (0.180 g, 0.32 mmol, Q36333, Isotec, Ohio, USA) was combined with 100 mL $H_2O$ in a 1 L flask. This ambient solution was then degassed with a rotary evaporator (model R-215 equipped with V-710 pump, Buchi, New Castle Del.) fitted with an $N_2$ (g) input, by decrementing the onboard pressure slowly to avoid boiling, from 70 to 25 mbar over approximately 10 minutes. The rhodium catalyst, bis(norbornadiene)rhodium (I) tetrafluoroborate (0.10 g, 0.27 mmol, 45-0230, CAS 36620-11-8, Strem Chemicals, Mass., USA) was dissolved in 7 mL acetone and was added drop-wise to the phosphine ligand solution to limit undesirable precipitation. After repeating the prior degassing procedure, this catalyst solution was mixed with 2-hydroxyethyl acrylate-1-$^{13}$C,2,3,3-$d_3$ (HEA, 97% chemical purity, 99 atom % $^{13}$C, 98 atom % D (20 mg, 0.16 mmol, Sigma-Aldrich 676071) in a 150 mL square bottle (431430, Corning Life Sciences, N.Y., USA).

Solutions containing unsaturated precursor molecules, catalyst, and ligand prepared as described above, were then connected to a previously described automated parahydrogen polarizer, (see, Waddell, K. W.; Coffey, A. M.; Chekmenev, E. Y. *J. Am. Chem.* 2011, 133, 97-101 and International Patent Application Pub. No. WO 2012/145733, each of which is incorporated herein in its entirety by reference) equipped with a dual-tuned $^1H/^{13}C$ coil. See, Coffey, A. M.; Shchepin, R. V.; Wilkens, K.; Waddell, K. W.; Chekmenev, E. Y. *Journal of Magnetic Resonance* 2012, 220, 94-101, which is incorporated herein in its entirety by reference. Briefly, the chemical reaction was pulse programmed with a commercial NMR console (model KEA, Magritek NZ), to synchronize chemical reaction parameters, decoupling fields, polarization transfer sequences, and detection of NMR signals. PASADENA precursors were sprayed remotely into a plastic (polysulfone) reactor located within a 48 mT static magnetic field. The external solution was equilibrated at 65° C. prior to spraying, and 16.5 bar (240 psi) nitrogen gas was used to inject this heated PASADENA precursor solution into a pressurized atmosphere of 7 bar (100 psi) parahydrogen. Immediately following injection, proton continuous wave decoupling was applied at a frequency of 2.02 MHz ($B_0$=47.5 mT) with a magnitude of 5 kHz. This decoupling field was maintained for 4 seconds to lock the parahydrogen spin ensemble while the hydrogenation reaction went to completion.

The pulse sequences for transferring polarization were applied immediately after continuous wave decoupling was turned off (FIG. 2). For the HEP molecule, the $t_1$, $t_2$, $t_3$, and $t_4$ intervals were 9.75, 50.34, 36.20, and 28.28 ms, respectively, calculated by inverting the density matrix expressions above (see Theory) assuming a proton-proton coupling of 7.57 Hz, and a carbon-proton scalar coupling asymmetry of 12.86 Hz. See, Goldman, M.; Johannesson, H.; Axelsson, O.; Karlsson, M. *Magn Reson Imaging* 2005, 23, 153-7, which is incorporated herein in its entirety by reference. The actual couplings could vary somewhat from these values depending on pH and specific attributes of the polarization process such as temperature and pressure. After polarization transfer, a single free induction decay was acquired with 512 points at a receiver bandwidth of 5 kHz, for a digital resolution of ~10 Hz per point.

Described here is a new pulse sequence for prolonging the effective lifetime of parahydrogen spin order in PHIP experiments performed at low magnetic fields in the strong-coupling regime of protons. The sequence transforms parahydrogen spin order efficiently into heteronuclear magnetization approximately independent of scalar coupling topology in three spin moieties (AA'X). This is a ubiquitous moiety in PHIP, being formed for example in current metabolic imaging agents such as the parahydrogen addition product of fumaric acid (succinate 1-$^{13}$C-2,3-$d_2$, see, Chekmenev, E. Y.; Hovener, J.; Norton, V. A.; Harris, K.; Batchelder, L. S.; Bhattacharya, P.; Ross, B. D.; Weitekamp, D. P. *J Am Chem Soc* 2008, 130, 4212-3, which is incorporated herein in its entirety by reference), and more recently in the ester analog (diethyl succinate 1-$^{13}$C-2,3-$d_2$, see, Zacharias, N. M.; Chan, H. R.; Sailasuta, N.; Ross, B. D.; Bhattacharya, P. *Journal of the American Chemical Society* 2012, 134, 934-943, which is incorporated herein in its entirety by reference). This sequence features two asymmetric proton refocusing intervals positioned about a heteronuclear excitation pulse to provide four unique delays ($t_1$-$t_4$), which in turn are optimized for the sequential conversion of parahydrogen spin order into heteronuclear magnetization (FIG. 2). The equations governing evolution of the density operator in each interval were described (see Theory) and are linked via equation numbers to FIG. 2 to provide an overall schematic of spin order flow from the initial singlet-state to the coupled heteronucleus. The shorthand hyper-SHIELDED (Singlet to Heteronuclei by Iterative Evolution Locks Dramatic Enhancement for Delivery) was adopted for quick reference due to the protective effect on PHIP hyperpolarization.

The analysis of spin dynamics under the influence of hyper-SHIELDED assumed strongly coupled protons and weak heteronuclear scalar couplings (Eq. 1), with the initial parahydrogen density operator retained without truncation and proportional to $I_1 \cdot I_2$ (Eq. 2). Chemical shifts were not considered because the effects are small compared to homonuclear proton couplings at targeted fields in the vicinity of 12 mT or lower, and additionally because offsets were refocused with 180° pulses on both channels placed at ¼ and ¾ of each evolution interval. See, Goldman, M.; Johannesson, H.; Axelsson, O.; Karlsson, M. *Magn Reson Imaging* 2005, 23, 153-7, which is incorporated herein in its entirety by reference. Relative to (truncated) high field density operators proportional to $I_{1z}I_{2z}$, evolution of the low field parahydrogen density operator is more complex and more efficient in terms of nominal heteronuclear polarization yield. The time-scale for transferring polarization to a heteronucleus is inversely proportional to the coupling asymmetry and approaches an asymptote in the limit that the parahydrogen addition product becomes symmetric.

The hyper-SHIELDED sequence was applied immediately following a period of initial proton decoupling, used to maintain equivalence of the parahydrogen protons and thus freeze evolution of the spin density operator (see, Goldman, M.; Johannesson, H. *Comptes Rendus Physique* 2005, 6, 575-581, which is incorporated herein in its entirety by reference) until the hydrogenation reaction goes to completion (FIG. 2). After this period of decoupling and chemical addition, the initial density matrix evolves from the parahydrogen singlet-state (Eq. 2) to three terms (Eq. 3a-c, symbols 3a-c in FIG. 2) in the Cartesian product basis (see, Sorensen, O. W.; Eich, G. W.; Levitt, M. H.; Bodenhausen, G.; Ernst, R. R. *Progress in Nuclear Magnetic Resonance Spectroscopy* 1983, 16, 163-192, which is incorporated herein in its entirety by reference) during the first interval ($t_1$). A 180° proton x-pulse then focuses these three terms of the density matrix into term 4c during the interval $t_2$. A 90° y-pulse on the S-nucleus (e.g. carbon-13) then allows term 4c to evolve into an additional three terms (symbols 6a-c, FIG. 2) during the interval $t_3$. Following a proton 180° pulse, these three terms (symbols 6a-c, FIG. 2) collapse into a single term during $t_4$ (symbol 7b, FIG. 2). This 7b term represents pure S-magnetization (see Eq. 7b), and can be either rotated to the longitudinal axis for storage with a 90° x-pulse, or left unperturbed in the transverse plane for detection in situ. See, Waddell, K. W.; Coffey, A. M.; Chekmenev, E. Y. *J. Am. Chem.* 2011, 133, 97-101, which is incorporated herein in its entirety by reference. As noted previously, refocusing at the center of the evolution intervals was insufficient to correct for field inhomogeneities and therefore nonselective refocusing pulses on both channels were interleaved at ¼ and ¾ duration of each evolution interval to refocus offsets and mitigate the deleterious impact of static field inhomogeneities.

A primary advantage of hyper-SHIELDED is that polarization yield is obtained approximately independent of coupling topology (FIG. 3), and this nearly uniform response of polarization is obtained without piecewise construction or recursive application of the sequence. See, Goldman, M.; Johannesson, H.; Axelsson, O.; Karlsson, M. *Magn Reson Imaging* 2005, 23, 153-7, which is incorporated herein in its entirety by reference. The difficulty of attaining uniform transfer efficiency in the conversion of parahydrogen spin order into heteronuclear magnetization can be appreciated qualitatively by comparison to familiar polarization transfer sequences such as INEPT (see, Morris, G. A.; Freeman, R. *Journal of the American Chemical Society* 1979, 101, 760-762, which is incorporated herein in its entirety by reference) or HMQC (see, Muller, L. *Journal of the American Chemical Society* 1979, 101, 4481-4484, which is incorporated herein in its entirety by reference). In conventional sequences, transverse magnetization in coupled AA'X spin systems evolve towards antiphase terms regardless of coupling asymmetry. By contrast, the parahydrogen singlet state formed with PASADENA becomes stationary in the limit that AA'X collapses to $A_2X$, as seen from Eq. 3 by substituting $\Delta=0$ (giving $\cos(\theta)=0$ and $\sin(\theta)=1$). For additional detail on the theoretical aspects of PHIP, we refer readers to recent reviews by Green and coworkers (Green, R. A.; Adams, R. W.; Duckett, S. B.; Mewis, R. E.; Williamson, D. C.; Green, G. G. R. *Progress in Nuclear Magnetic Resonance Spectroscopy* 2012, which is incorporated herein in its entirety by reference) and Natterer et al. (Natterer, J.; Bargon, J. *Progress in Nuclear Magnetic Resonance Spectroscopy* 1997, 31, 293-315, which is incorporated herein in its entirety by reference).

Figure 3:
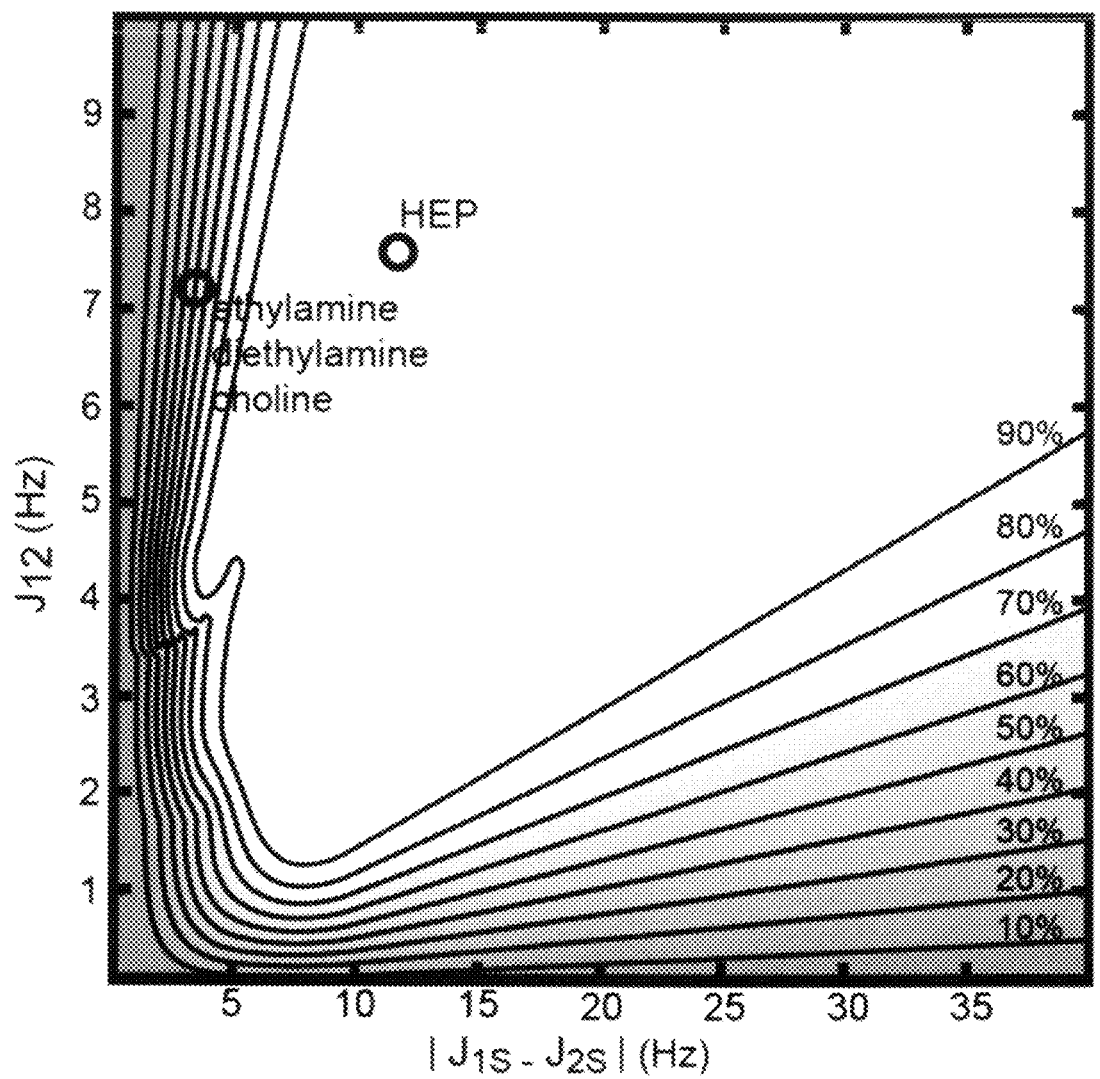
FIG. 3 is a graph of the polarization yield as a function of homonuclear proton coupling ($J_{12}$) for hyper-SHIELDED.

The nominal sensitivity of hyper-SHIELDED transfer efficiency was mapped to scalar coupling topology across a range of conceivable PASADENA addition products. For each unique set of couplings ($J_{12}$, $|J_{1S}-J_{2S}|$), the density matrix equations (see Theory) were inverted to solve for the optimal set of evolution intervals. Coupling asymmetry ($|J_{1S}-J_{2S}|$) and homonuclear proton couplings ($J_{12}$) were varied from 0 Hz to 45 Hz and 0 Hz to 10 Hz, respectively, against a total pulse sequence duration constraint of 300 ms (FIG. 3). As illustrated in FIG. 3, the transition from zero to uniformly efficient transfer with hyper-SHIELDED is steep. Heteronuclear polarization saturates on a broad plateau of uniform efficiency with as little as 8 Hz coupling asymmetry. Then as coupling asymmetry increases toward 35 Hz, homonuclear proton couplings must increase to maintain uniform efficiency.

This saturation plateau would expand if the total pulse sequence duration constraint was increased from 300 ms if application warranted, although the sequence was designed in particular to improve efficiency in the low asymmetry regime and therefore improve polarization yield in nitrogen-15 labeled PHIP addition products such as ethylamine, diethylamine, and choline which are known to have small asymmetries. In other words, without wishing to be bound by any particular theory, the total pulse sequence duration constraint of 300 ms causes less than maximum magnetization transfer with certain J-coupling asymmetries, but were the constraint removed, the magnetization transfer could be maximized given sufficient pulse duration.

Example 2

Experimental Verification of Hyper-SHIELDED Pulse Sequence and Comparative Pulse Sequence To highlight the performance of hyper-SHIELDED in nearly symmetric PHIP products, optimal efficiency was compared experimentally to a widely used transfer sequence (hereinafter, "GPS") previously reported by Goldman and coworkers (see, Goldman, M.; Johannesson, H.; Axelsson, O.; Karlsson, M. *Magn Reson Imaging* 2005, 23, 153-7, which is incorporated herein in its entirety by reference). GPS provided a convenient test point given that it was already implemented in a non-recursive version on our pulse programmable polarizer. See, Waddell, K. W.; Coffey, A. M.; Chekmenev, E. Y. *J. Am. Chem.* 2011, 133, 97-101, which is incorporated herein in its entirety by reference. Although not yet experimentally demonstrated, it is noted that a series of three piecewise optimal solutions were recently reported by Kadlecek and coworkers. See, Kadlecek, S.; Emami, K.; Ishii, M.; Rizi, R. *J Magn Reson* 2011, 205, 9-13, which is incorporated herein in its entirety by reference. This set of sequences may offer solutions to the transfer problem in three distinct coupling asymmetry epochs, but utilizes a different pulse sequence for each epoch. In other words, the pulse sequence cannot be adapted to transfer nuclear singlet state spin order into heteronuclear magnetization localized on S at any $|J_{1S}-J_{2S}|$ when the independent evolution intervals are optimized. A possible disadvantage of this sequences reported by Kadlecek and coworkers is that the scalar couplings present in the reactor are not often known precisely at the reaction conditions, and can differ significantly from separate determination from high resolution NMR results obtained at nearly equivalent pH. In other words, if the scalar couplings present in the reactor differ from separate determination from high resolution NMR results, then optimizing magnetization transfer could require the use of a different pulse sequence from a different coupling asymmetry epoch. It is often necessary to empirically optimize transfer sequences to obtain best results, and this is made easier with evolution intervals that can be adjusted along a continuum within a consolidated sequence such as hyper-SHIELDED.

Figure 4:
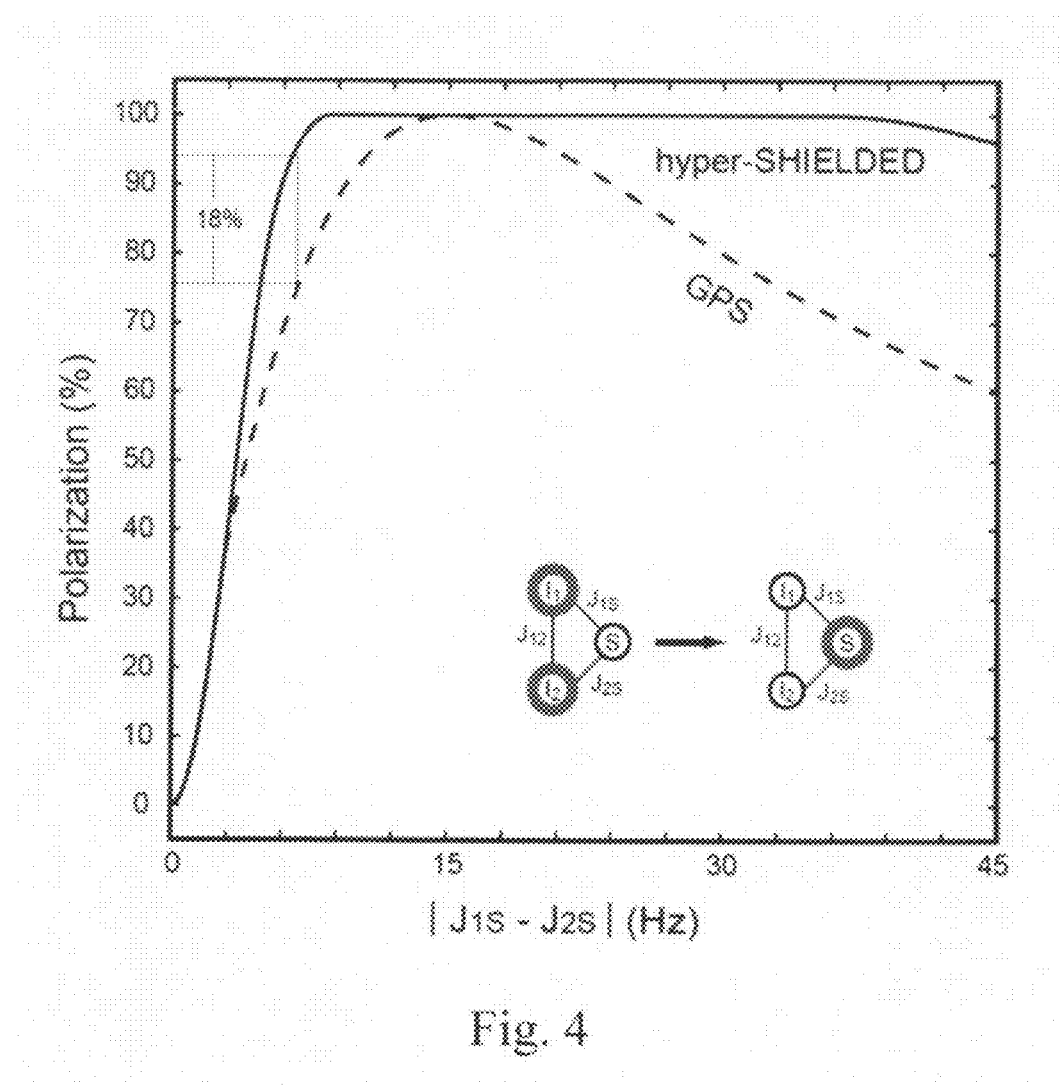
FIG. 4 is a graph of theoretical maximized polarization transfer efficiency versus heteronuclear coupling asymmetry comparing the hyper-SHIELDED pulse sequence (solid) to a non-recursive implementation of the GPS comparison sequence of Example 2.
Figure 5:
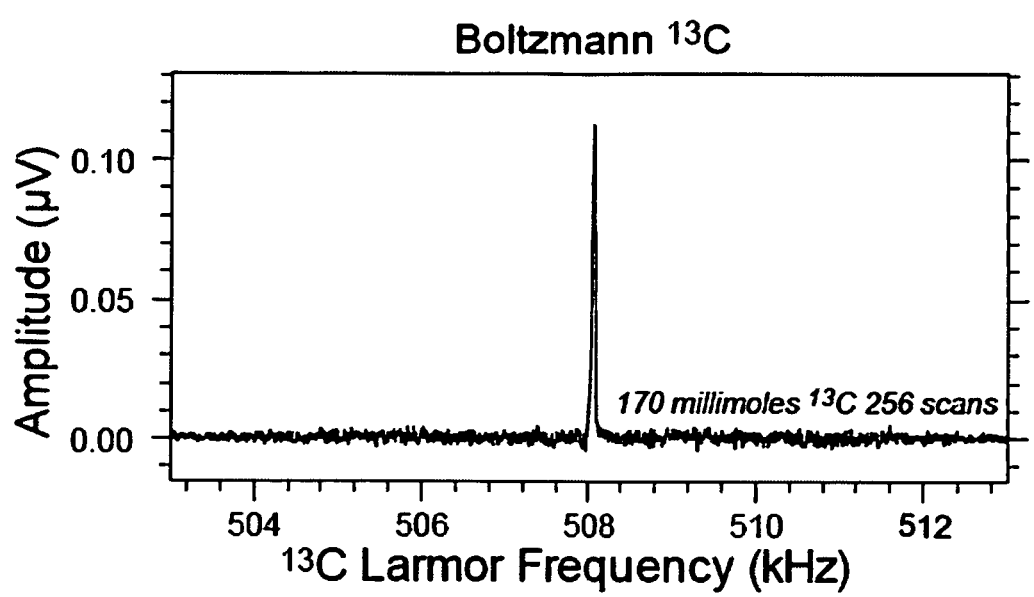
FIG. 5 is a Boltzmann polarized carbon-13 spectrum acquired from an aqueous solution containing 170 millimoles of the reaction product 2-hydroxy, 1-$^{13}$C-ethylpropionate-$d_3$ (HEP).
Figure 6:
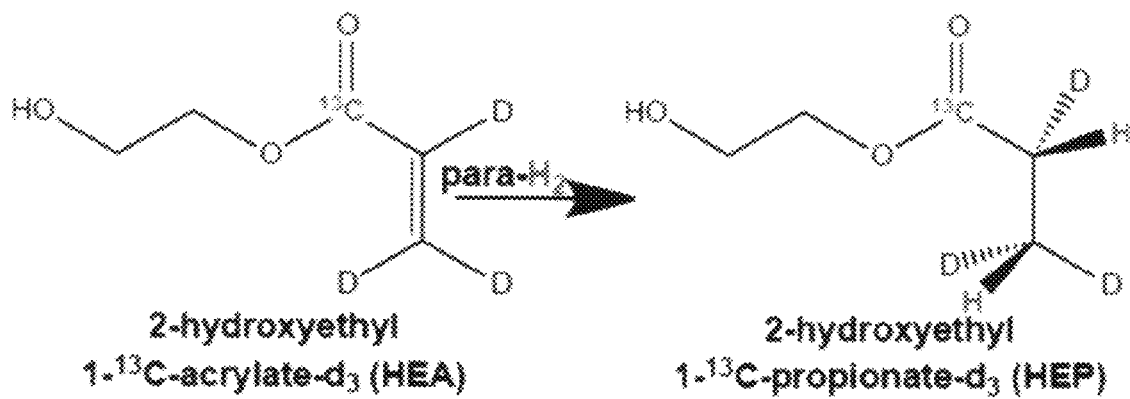
FIG. 6 is a reaction schematic for synthesizing parahydrogenated 2-hydroxy, 1-$^{13}$C-ethylpropionate-$d_3$ (HEP).
Figure 7:
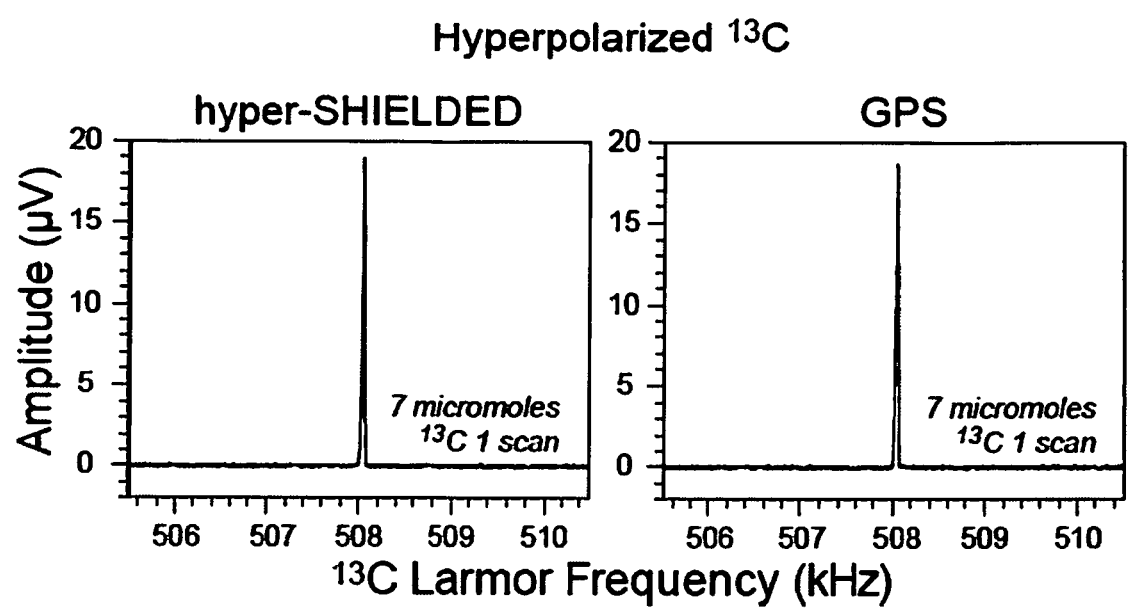
FIG. 7 are experimentally determined yields for the hyper-SHIELDED pulse sequence (left) and the GPS comparison sequence (right) of Example 2.

For comparison with the experimentally validated GPS sequence, density matrix equations for both sequences were inverted to find the optimal evolution intervals that maximize polarization yield as a function of coupling asymmetry at a common proton coupling ($J_{12}$) of 7.5 Hz. As illustrated in FIG. 3, the dependence of polarization yield in the small asymmetry regime is relatively insensitive to $J_{12}$. We found that polarization yields reach uniform efficiency more rapidly as a function of asymmetry in hyper-SHIELDED versus the non-recursive application of GPS (see, Goldman, M.; Johannesson, H. *Comptes Rendus Physique* 2005, 6, 575-581, which is incorporated herein in its entirety by reference), and high levels of polarization are sustained across a broad range of asymmetries (FIG. 4). For the PASADENA product, 2-hydroxy, 1-$^{13}$C-ethylpropionate-$d_3$, hyper-SHIELDED was predicted to be equivalent to GPS, and this was verified experimentally (FIGS. 5-7), where a factor of 5,000,000 enhancement was obtained at a static field of 48 mT. Hyper-SHIELDED is predicted to give approximately 18 percent higher polarization yield for the biologically important class of nitrogen-15 labeled PASADENA products such as ethylamine, diethylamine, and choline. The use of four independent evolution intervals enables fast saturation of polarization as a function of spin-system asymmetry, and provides nearly uniform efficiency over a broad range in a consolidated sequence without requiring recursive application, hence providing a streamlined and broadly efficient transfer sequence.

The text that follows is the hyper-SHIELDED minimization code:

```
function tau = Pump(J)
% Calculating the time delays for hS3
% t = array of time delays (4 delays)
% J(1) = proton-proton coupling
% J(2) and J(3) = proton-carbon couplings
delta = (J(2)-J(3))/(2*J(1));
theta = asin(1/(sqrt(1+delta^2)));
omega = J(1)*(sqrt(1+delta^2));
   for k=1:1000;
      t1=0.0001*k;
      for l=1:1000;
         t2=0.0001*l;
         F(k,l) = abs(-0.5*sin(2*theta)*(cos(2*theta)...
           +2*((sin(theta))^2)*cos(2*pi*omega*t2)...
           -2*((cos(theta))^2)*cos(2*pi*omega*t1)...
           +cos(2*theta)*cos(2*pi*omega*t1)*cos(2*pi*omega*t2)...
           +sin(2*pi*omega*t1)*sin(2*pi*omega*t2)));
      end
   end
[K,L] = find(F>(max(F(:))-0.0001));
len=length(K);
for n=1:len;
   Dur(n)=K(n)+L(n);
end
[minDur,N]=find(Dur==min(Dur));
tau(1)=K(min(N))*0.0001;
tau(2)=L(min(N))*0.0001;
P(1)=F(K(min(N)),L(min(N)));
for k=1:1000;
   t3=0.0001*k;
   for l=1:1000;
      t4=0.0001*l;
      F(k,l) =
         abs(cos(theta)*cos(2*pi*omega*t3)*sin(2*pi*omega*t4)...
         -sin(theta)*sin(2*theta)*sin(2*pi*omega*t3)...
         -cos(theta)*cos(2*theta)*sin(2*pi*omega*t3)...
         *cos(2*pi*omega*t4));
   end
end
[K,L] = find(F>(max(F(:))-0.0001));
len=length(K);
for n=1:len;
   Dur(n)=K(n)+L(n);
end
[minDur,N]=find(Dur==min(Dur));
tau(3)=K(min(N))*0.0001;
tau(4)=L(min(N))*0.0001;
P(2)=F(K(min(N)),L(min(N)));
t1=tau(1);
t2=tau(2);
t3=tau(3);
t4=tau(4);
tau(5)=P(1)*P(2);
tau(6)=abs((sin(theta)*sin(2*theta)*sin(2*pi*omega*t2)...
   +cos(theta)*cos(2*theta)*cos(2*pi*omega*t1)*sin(2*pi*omega*t2)...
   -cos(theta)*sin(2*pi*omega*t1)*cos(2*pi*omega*t2))...
   *(0.25*sin(4*theta)...
   +0.25*sin(4*theta)*cos(2*pi*omega*t3)*cos(2*pi*omega*t4)...
   +sin(2*theta)*(((sin(theta))^2)*cos(2*pi*omega*t3)...
   -((cos(theta))^2)*cos(2*pi*omega*t4))...
   +cos(theta)*sin(theta)*sin(2*pi*omega*t3)*sin(2*pi*omega*t4))...
   -0.5*sin(2*theta)*(cos(2*theta)...
   +2*((sin(theta))^2)*cos(2*pi*omega*t2)...
   -2*((cos(theta))^2)*cos(2*pi*omega*t1)...
   +cos(2*theta)*cos(2*pi*omega*t1)*cos(2*pi*omega*t2)...
   +sin(2*pi*omega*t1)*sin(2*pi*omega*t2))...
   *(cos(theta)*cos(2*pi*omega*t3)*sin(2*pi*omega*t4)...
   -sin(theta)*sin(2*theta)*sin(2*pi*omega*t3)...
   -cos(theta)*cos(2*theta)*sin(2*pi*omega*t3)*cos(2*pi*omega*t4)));
end
```

What is claimed is:

1. A method of performing Nuclear Magnetic Resonance (NMR) spectroscopy or Magnetic Resonance Imaging (MRI), the method comprising:
   a) generating a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$;
   b) transferring the nuclear singlet state spin order into heteronuclear magnetization localized on S by applying a single, non-recursive pulse sequence at a low magnetic field in the strong coupling regime of protons; and
   c) performing NMR spectroscopy or MRI with the compound comprising heteronuclear magnetization localized on S,
   wherein $|J_{1S}-J_{2S}|$ is non-zero,
   wherein the pulse sequence comprises a plurality of sequential radio frequency pulses separated by independent evolution intervals,
   wherein the pulse sequence transfers at least about 75% of the nuclear singlet state spin order into heteronuclear magnetization localized on S at any $|J_{1S}-J_{2S}|$ when the independent evolution intervals are optimized, and
   wherein the pulse sequence comprises the following sequential steps:
      a) waiting a time $t_1$ after generating the compound;
      b) applying a 180(+x) pulse on $I_1$ and $I_2$;
      c) waiting a time $t_2$;
      d) applying a 90(+y) pulse on S;
      e) waiting a time $t_3$;
      f) applying a 180(+x) pulse on $I_1$ and $I_2$;
      g) waiting a time $t_4$; and
      h) applying a 90(+x) pulse on S.

2. The method of claim 1, wherein generating a compound comprises hyperpolarizing the compound by parahydrogen induced polarization (PHIP).

3. The method of claim 1, wherein the compound has a Hamiltonian of $$H=2\pi[J_{12}(I_1 \cdot I_2)+J_{1S}I_{1z}S_z+J_{2S}I_{2z}S_z].$$

4. The method of claim 1, wherein the pulse sequence comprises a first portion and a second portion, wherein the first portion converts the nuclear singlet state spin order localized on $I_1$ and $I_2$ into a pure state which is coupled to S, and wherein the second portion converts the pure state which is coupled to S into longitudinal net magnetization on S.

5. The method of claim 1, wherein $t_1$, $t_2$, $t_3$ and $t_4$ are selected to maximize transfer of the nuclear singlet state spin order localized on $I_1$ and $I_2$ into longitudinal net magnetization on S.

6. The method of The method of claim 1, wherein $t_1$ and $t_2$ are selected to maximize transfer of the nuclear singlet state spin order localized on $I_1$ and $I_2$ into a pure state which is coupled to S, and wherein $t_3$ and $t_4$ are selected to maximize transfer of the pure state which is coupled to S into longitudinal net magnetization on S.

7. The method of claim 1, wherein the pulse sequence transfers at least about 90% of the nuclear singlet state spin order into heteronuclear magnetization localized on S at any $|J_{1S}-J_{2S}|$ when the independent evolution intervals are optimized.

8. An NMR spectroscopy or MRI system configured to perform the method of claim 1.

9. A method of performing Nuclear Magnetic Resonance (NMR) spectroscopy or Magnetic Resonance Imaging (MRI), the method comprising:
   a) generating a compound comprising a first nuclear species ($I_1$), a second nuclear species ($I_2$), a third nuclear species (S), a heteronuclear coupling asymmetry ($|J_{1S}-J_{2S}|$) and nuclear singlet state spin order localized on $I_1$ and $I_2$;
   b) transferring the nuclear singlet state spin order into heteronuclear magnetization localized on S by applying a single, non-recursive pulse sequence at a low magnetic field in the strong coupling regime of protons; and
   c) performing NMR spectroscopy or MRI with the compound comprising heteronuclear magnetization localized on S;
wherein $|J_{1S}-J_{2S}|$ is non-zero,
wherein the pulse sequence comprises a plurality of sequential radio frequency pulses separated by independent evolution intervals,
wherein the pulse sequence transfers at least about 75% of the nuclear singlet state spin order into heteronuclear magnetization localized on S at an $|J_{1S}-J_{2S}|$ when the independent evolution intervals are optimized, and
wherein the hyperpolarized sample further comprises a fourth nuclear species (R), and wherein the pulse sequence comprises the following sequential steps:
   a) waiting a time $t_1$ after generating the compound;
   b) applying a 180(+x) pulse on S;
   c) waiting a time $t_2$;
   d) applying a 180(+x) pulse on $I_1$ and $I_2$;
   e) waiting a time $t_3$;
   f) applying a 90(+y) pulse on S;
   g) waiting a time $t_4$;
   h) applying a 180(+x) pulse on S;
   i) waiting a time $t_5$;
   j) applying a 180(+x) pulse on $I_1$ and $I_2$;
   k) waiting a time $t_6$; and
   l) applying a 90(+x) pulse on S.

10. The method of claim 9, wherein $t_1$, $t_2$, $t_3$, $t_4$, $t_5$ and $t_6$ are selected to maximize transfer of the nuclear singlet state spin order localized on $I_1$ and $I_2$ into longitudinal net magnetization on S.

11. The method of claim 9, wherein $t_1$, $t_2$ and $t_3$ are selected to maximize transfer of the nuclear singlet state spin order localized on $I_1$ and $I_2$ into a pure state which is coupled to S, and wherein $t_4$, $t_5$ and $t_6$ are selected to maximize transfer of the pure state which is coupled to S into longitudinal net magnetization on S.

12. A method of performing Nuclear Magnetic Resonance (NMR) spectroscopy or Magnetic Resonance Imaging (MRI), the method comprising:
   a) generating a compound comprising a first nuclear species ($I_1$), a second nuclear species ($I_2$), a third nuclear species (S), a fourth nuclear species (R) and a nuclear singlet state spin order localized on $I_1$ and $I_2$;
   b) transferring the nuclear singlet state spin order into heteronuclear magnetization localized on S by applying a pulse sequence at a low magnetic field in the strong coupling regime of protons; and
   c) performing NMR spectroscopy or MRI with the compound comprising heteronuclear magnetization localized on S;
wherein the pulse sequence comprises the following sequential steps:
   a) waiting a time $t_1$ after hyperpolarizing the sample;
   b) applying a 180(+x) pulse on S;
   c) waiting a time $t_2$;
   d) applying a 180(+x) pulse on $I_1$ and $I_2$;
   e) waiting a time $t_3$;
   f) applying a 90(+y) pulse on S;
   g) waiting a time $t_4$;
   h) applying a 180(+x) pulse on S;
   i) waiting a time $t_5$;
   j) applying a 180(+x) pulse on $I_1$ and $I_2$;
   k) waiting a time $t_6$; and
   l) applying a 90(+x) pulse on S.

13. The method of claim 12, wherein the compound has a Hamiltonian of $$H=2\pi[J_{12}(I_{1x}I_{2x}+I_{1y}I_{2y}+I_{1z}I_{2z})+J_{1S}I_{1z}S_z+J_{1R}I_{1z}R_z+J_{2S}I_{2z}S_z+J_{2R}I_{2z}R_z+J_{SR}S_zR_z].$$

14. The method of claim 12, wherein $t_1$, $t_2$, $t_3$, $t_4$, $t_5$ and $t_6$ are selected to maximize transfer of the nuclear singlet state spin order localized on $I_1$ and $I_2$ into longitudinal net magnetization on S.

15. The method of claim 12, wherein $t_1$, $t_2$ and $t_3$ are selected to maximize transfer of the nuclear singlet state spin order localized on $I_1$ and $I_2$ into a pure state which is coupled to S, and wherein $t_4$, $t_5$ and $t_6$ are selected to maximize transfer of the pure state which is coupled to S into longitudinal net magnetization on S.

16. A method of performing Nuclear Magnetic Resonance (NMR) spectroscopy or Magnetic Resonance Imaging (MRI), the method comprising:
   a) determining J-couplings for a compound comprising a first nuclear species ($I_1$), a second nuclear species ($I_2$), a third nuclear species (S), a heteronuclear coupling asymmetry ($|J_{1S}-J_{2S}|$) and a nuclear singlet state spin order localized on $I_1$ and $I_2$;
   b) calculating optimal evolution intervals for a single, non-recursive pulse sequence at low magnetic field in the strong coupling regime of protons using the J-couplings, the pulse sequence comprising a sequential plurality of radio frequency pulses separated by independent evolution intervals;

c) generating the compound;
d) transferring the nuclear singlet state spin order into heteronuclear magnetization localized on S by applying the pulse sequence with optimal evolution intervals to the compound; and
e) performing NMR spectroscopy or MRI with the compound comprising heteronuclear magnetization localized on S, wherein $|J_{1S}-J_{2S}|$ is non-zero,
wherein the pulse sequence transfers at least about 75% of the nuclear singlet state spin order into heteronuclear magnetization localized on S at any $|J_{1S}-J_{2S}|$, and
wherein calculating optimal evolution intervals comprises inverting a density matrix expression representing the evolution of spin states of the compound during application of the pulse sequence to the compound, minimizing the difference between a density matrix expression representing the evolution of spin states of the compound during application of the pulse sequence and a desired state which is coupled to S, or a combination thereof.

17. The method of claim 16, wherein determining J-couplings for a compound comprises experimentally determining J-couplings, theoretically calculating J-couplings and combinations thereof.

* * * * *

UNITED STATES PATENT AND TRADEMARK OFFICE
CERTIFICATE OF CORRECTION

PATENT NO. : 9,566,354 B2
APPLICATION NO. : 13/998342
DATED : February 14, 2017
INVENTOR(S) : Kevin Waddell et al.

It is certified that error appears in the above-identified patent and that said Letters Patent is hereby corrected as shown below:

In the Specification

Column 1, Line 13:
Replace the following paragraph:
[[This invention was made with government support from ICMIC 5P50 CA128323-03. The United States federal government has certain rights in this invention.]]

With the paragraph:
--This invention was made with government support under Grant nos. CA128323 and CA136440, awarded by the National Institutes of Health. The government has certain rights to this invention.--

Signed and Sealed this
Eleventh Day of July, 2023

Katherine Kelly Vidal
*Director of the United States Patent and Trademark Office*